United States Patent [19]

Hodek et al.

[11] Patent Number: 4,683,344

[45] Date of Patent: Jul. 28, 1987

[54] PROCESS FOR THE PREPARATION OF AN ORGANOMAGNESIUM COMPOUND

[75] Inventors: Robert B. Hodek, Gibsonia; Jerome A. Seiner, Pittsburgh, both of Pa.

[73] Assignee: PPG Industries, Inc., Pittsburgh, Pa.

[21] Appl. No.: 690,443

[22] Filed: Jan. 11, 1985

Related U.S. Application Data

[63] Continuation-in-part of Ser. No. 575,089, Jan. 30, 1984, Pat. No. 4,508,646.

[51] Int. Cl.$^4$ ............... C07C 39/00; C07C 39/02; C07C 39/04
[52] U.S. Cl. ............... 568/716; 568/675; 568/763; 568/851
[58] Field of Search ............ 260/239.3 R; 568/716, 568/763, 851, 675

[56] References Cited

U.S. PATENT DOCUMENTS

| | | | |
|---|---|---|---|
| 2,555,599 | 6/1951 | Newman | 568/675 |
| 3,018,273 | 1/1962 | Butler et al. | 260/78 |
| 3,439,042 | 4/1969 | Eschinasi et al. | 568/851 X |
| 3,450,662 | 6/1969 | Tierney | 260/30.8 |
| 3,451,963 | 6/1969 | Tierney et al. | 260/37 |
| 4,370,257 | 1/1983 | Imai et al. | 568/851 X |
| 4,438,034 | 3/1984 | Garner | 260/239.3 |
| 4,508,646 | 4/1985 | Hodek et al. | 260/239.3 R |

FOREIGN PATENT DOCUMENTS 1167738 10/1969 United Kingdom .

OTHER PUBLICATIONS

Kharasch et al, Grignard Reactions of Nonmetallic Substances, Prentice-Hall, Inc. N.Y., pp. 1166–1174 (1954).

*Primary Examiner*—Helen M. S. Sneed
*Attorney, Agent, or Firm*—Linda Pingitore

[57] ABSTRACT

A process for the preparation of a pulverulent organomagnesium compound involves bringing together into intimate admixture a particulate hydroxyl functional material with an organomagnesium-containing material. The process is conducted at a temperature below the melting point of the hydroxyl functional material but at a temperature sufficient to convert at least a portion of the hydroxyl functional material to the pulverulent organomagnesium compound. The aforesaid organomagnesium compounds are useful as intermediates in generating anionic sites for anionic polymerization.

7 Claims, No Drawings

PROCESS FOR THE PREPARATION OF AN ORGANOMAGNESIUM COMPOUND

CROSS REFERENCE TO RELATED APPLICATION

This application is a continuation-in-part of Ser. No. 575,089, filed Jan. 30, 1984, now U.S. Pat. No. 4,508,646 entitled A PROCESS FOR THE PREPARATION OF A CATALYST USEFUL FOR ANIONIC LACTAM POLYMERIZATION.

BACKGROUND OF THE INVENTION

The present invention relates to the preparation of organomagnesium compounds which have a variety of uses.

Sometimes intermediates are required in the preparation of other compounds. For example, often in the synthesis of other materials it may be necessary to generatae an anionic site from an active hydrogen-containing material such as a hydroxyl group-containing material. This has generally been done by the addition of sodium hydroxide or potassium hydroxide which strips the proton from the hydroxyl group generating an anionic site on the oxygen and forming water which can be removed by distillation. Often, however, the particular active hydrogen may not be sufficiently reactive with a base such as sodium or potassium hydroxide and it becomes difficult to generate such anionic sites. There is a need therefore for an improved way of preparing these types of intermediates.

Moreover, heretofore, a class of organomagnesium compounds, lactam-magnesium compounds, have been prepared either by a process which requires heating of the lactam monomer and the organomagnesium material at elevated temperatures for an extended period in order to melt the lactam monomer, or by dissolving the lactam monomer in a solvent. These procedures are not without attendant difficulties. For example, heating of the lactam at an elevated temperature increases the probability that the lactam monomer will polymerize. Moreover, even when the process is successfully carried out, the catalyst product generally requires further mechanical processing such as grinding prior to use. Although dissolving the lactam monomer in a solvent prior to reaction with the organomagnesium-containing material saves energy because the need for heating of the lactam monomer to melt it is alleviated, the catalyst product still requires mechanical processing prior to use.

There is a need, therefore, for an improved method of preparing organomagnesium compounds which is simple, efficient, and economical and results in a product which can be utilized without mechanical processing prior to use.

SUMMARY OF THE INVENTION

In accordance with the present invention, there is provided a process for the preparation of pulverulent organomagnesium compounds such as lactam-magnesium compounds. The process comprises bringing together into intimate admixture a particulate hydroxyl functional material with an organomagnesium-containing material at a temperature below the melting point of the active hydroxyl functional material but at a temperature sufficient to convert at least a portion of the hydroxyl functional material to said pulverulent organomagnesium compound.

DETAILED DESCRIPTION OF THE INVENTION

Broadly stated, the process of the present invention comprises bringing into intimate admixture an active hydrogen-containing material in particulate form and an organomagnesium-containing material. The aforesaid components are brought together at a temperature below the melting point of the active hydrogen-containing material but at a temperature sufficient to convert at least a portion of the active hydrogen-containing material to organomagnesium compound in pulverulent form.

The particulate active hydrogen-containing material is preferably hydroxyl functional. Examples of suitable active hydrogen-containing materials include diphenyl carbinol; triphenyl carbinol; pentaerythritol; dipentaerythritol; polyethylene oxide; polypropylene oxide; 2,6-diphenyl phenol; 5-phenyl-1-pentanol; phenylphenol; neopentyl glycol and 4,4'-isopropylidenediphenol (Bisphenol A). Also useful herein are polyamides and the like.

In a further preferred embodiment, the active hydrogen-containing material is a lactam monomer in particulate form. Suitable lactam monomers can be represented by the following structural formula:

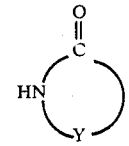

wherein Y is an alkylene group having from 3 to 12 carbon atoms. Examples of suitable lactams include butyrolactam, valerolactam, epsilon-caprolactam, laurolactam, 2-pyrrolidinone, and 2-azocyclotridecanone. Preferably, epsilon-caprolactam is utilized.

In the event that the desired active hydrogen-containing material is not normally in particulate form, e.g., a solid or a liquid, it can nevertheless be utilized in the claimed process. The liquid active hydrogen-containing mataerial can be readily converted to particulate form by, for example, freezing and then pulverizing the resultant solid. A solid material can, of course, be particulated by pulverizing it.

The organomagnesium-containing material is preferably an organomagnesium halide. Exemplary of these preferred materials are Grignard reagents. Suitable Grignard reagents include a large variety of materials which are commercially available, for example, allyl magnesium chloride; benzyl magnesium chloride; n-butyl magnesium chloride; sec-butyl magnesium chloride; p-chlorophenyl magnesium chloride, cyclohexyl magnesium chloride, ethyl magnesium chloride, isopropyl magnesium chloride, methyl magnesium chloride, phenyl magnesium chloride, n-propyl magnesium chloride, o-tolyl magnesium chloride, vinyl magnesium chloride; ethyl magnesium bromide, methyl magnesium bromide and n-octyl magnesium chloride. Preferably, ethyl magnesium bromide, benzyl magnesium chloride, and methyl magnesium bromide are utilized. Other organomagnesium-containing materials such as dibutyl magnesium are also useful herein. The Grignard reagents utilized herein are usually in the presence of ether or other solvent.

The particulate active hydrogen-containing material and organomagnesium-containing material are brought into intimate admixture at a temperature below the melting point of the active hydrogen-containing material but at a temperature sufficient for reaction between the active hyrogen-containing material and the organomagnesium-containing material. For example, when a lactam such as epsilon-caprolactam is utilized as the active hydrogen-containing material, the temperature is generally at least 0° C. Usually, however, the process of the present invention is carried out at ambient temperature. Admixture can be accomplished in a variety of ways although it is typically accomplished by vigorously agitating the materials together by means of a mechanical stirring or propelling device. The resultant reaction mixture is a heterogeneous mixture. The reaction is believed to be complete and pulverulent organomagnesium compound formed upon termination of the exotherm which results upon admixture of the organomagnesium-containing material and the particulate active hydrogen-containing material. The process of the present invention can be termed a "solid state" preparation since the process is carried out without solubilizing or melting the active hydrogen-containing material. That is, it participates in the reaction as a solid without proceeding through a fluid state. It should be understood that this is the case even though the Grignard reagent is usually associated with ether or other solvent. The amount of ether or other solvent associated with the Grignard reagent is inadequate to solubilize the active hydrogen-containing material.

The term "solid state" also encompasses the embodiment of the present invetion wherein the particulate active hydrogen-containing material is in essentially dispersed form in a diluent prior to admixture with the organomagnesium-containing material. Materials which are essentially non-solvents for the particulate active hydrogen-containing material and final pulverulent product are preferred as diluents. The particular choice of non-solvent will depend upon the particular particulate active hydrogen-containing material being utilized. It should be understood that in addition to having a low solubility for the particulate active hydrogen-containing material and the final product, the non-solvent should also be chosen so that it does not react with either of these materials. When the active hydrogen-containing material is a lactam, examples of suitable non-solvents include aliphatic hydrocarbons such as cyclopentane, cyclohexane, hexane, and heptane. For lactams aliphatic hydrocarbons such as cyclohexane are preferably utilized herein. Exemplary of organomagnesium compounds prepared according to the present invention are caprolactam magnesium bromide, laurolactam magnesium bromide, caprolactam magnesium chloride, neopentyl glycoxy magnesium bromide, and 4,4'-isopropylidenediphenoxy magnesium bromide.

The quantities of particulate active hydrogen-containing material and organomagnesium-containing material, preferably Grignard reagents which are utilized in the claimed process can vary depending upon the amount of theoretical conversion desired. That is, the amount, on a mole percent basis, of active hydrogen-containing material converted to organomagnesium compound. Generally, one mole of active hydrogen will react with one mole of organomagnesium-containing material to form the resultant organomagnesium compound. Quantities can be selected to yield theoretical conversions of up to 100 mole percent. For example, when the active hydrogen-containing material is a lactam, quantities are selected to yield theoretical conversions ranging from 15 mole percent to 50 mole percent. For example, in one embodiment, 100 moles of epsilon-caprolactam is reacted with 50 moles of ethyl magnesium bromide resulting in a theoretical conversion of 50 mole percent. Depending upon the percentage conversion, the resultant pulverulent product will have a corresponding quantity of unreacted particulate active hydrogen-containing material associated with it. The presence of this material does not detract from the properties of the final product but rather in some instances, it is believed to facilitate handling.

In the embodiment of the present invention wherein the particulate active hydrogen-containing material is in essentially dispersed form, preferably in a non-solvent, prior to admixture with the organomagnesium-containing material, the volume of non-solvent is adjusted to permit thorough mixing and agitation of the resultant dispersion.

Since the process of the present invention is conducted below the melting point of the active hydrogen-containing material, many advantages result. For the preparation of lactam-magnesium compound, the molten conditions of the prior art are avoided and the potential of lactam polymerization is reduced. Moreover, since the product is in the form of a dusty powder, it is directly usable without the necessity for further mechanical processing such as grinding. The claimed process is efficient, economical, and results in a pulverulent product with immediate usability without further processing.

The invention will be further described in connection with the examples which follow. These examples are given as illustrative of the invention and are not to be construed as limiting it to their details.

EXAMPLE I

This Example illustrates the preparation of a pulverulent organomagnesium compound according to the present invention.

| Ingredients | Amount |
| --- | --- |
| epsilon-caprolactam | 150 grams |
| ethyl magnesium bromide (2.9 molar in ether) | .92 milliliters |

The ethyl magnesium bromide was added to the epsilon-caprolactam in thirty milliliter aliquots over a period of an hour at a tempera ture of 32° C. After the addition was complete, the reaction product was vacuum stripped leaving the caprolactam magnesium bromide as a pulverulent residue. The theoretical conversion of lactam monomer to reaction product was 20 mole percent.

EXAMPLE II

This Example also illustrates the preparation of pulverulent organo magnesium compound according to the present invention. In the embodiment represented by this Example, the lactam monomer is dispersed in cyclohexane prior to admixture with the organomagnesium halide.

| Ingredients | Amount |
| --- | --- |
| epsilon-caprolactam | 125 grams |
| cyclohexane | 475 grams |
| ethyl magnesium bromide (2.9 Molar in ether) | 76.3 milliliters |

The epsilon-caprolactam was agitated together with the cyclohexane until a dispersion was formed. Subsequently, the ethyl magnesium bromide was added in 20 milliliter aliquots at such a rate that the reaction temperature was maintained below 45° C. After each aliquot addition, the mixture was placed in vacuo for five minutes. After the final aliquot addition, the cyclohexane was removed in vacuo leaving the caprolactam magnesium bromide reaction product as a white pulverulent residue. The theoretical conversion of lactam monomer to reaction product in this example was also 20 mole percent.

EXAMPLE III

This Example is similar to Example II, above, with the exception that benzyl magnesium chloride was used in place of ethyl magnesium chloride.

| Ingredients | Amount |
| --- | --- |
| epsilon-caprolactam | 113 grams |
| cyclohexane | 500 grams |
| benzyl magnesium chloride (2 Molar in tetrahydrofuran) | 100 milliliters |

The epsilon-caprolactam was agitated together with 400 grams of the cyclohexane until a dispersion was formed. Subsequently, the benzyl magnesium chloride was added in 25 milliliter aliquots. After each aliquot addition, the mixture was placed in vacuo for five minutes. After the final aliquot, an additional 100 grams of cyclohexane was added and the reaction mixture placed in vacuo to remove the cyclohexane leaving the caprolactam magnesium chloride reaction product as a pulverulent residue. The theoretical conversion of lactam monomer to reaction product in this example was also 20 mole percent.

EXAMPLE IV

This Example is similar to Example II, above, with the exception that the theoretical conversion of lactam monomer to reaction product was 50 mole percent.

| Ingredients | Amount |
| --- | --- |
| epsilon-caprolactam | 100 grams |
| cyclohexane | 500 grams |
| ethyl magnesium bromide (2.9 Molar in ether) | 152.6 milliliters |

The epsilon-caprolactam was agitated together with the cyclohexane until a dispersion was formed. Subsequently, the ethyl magnesium bromide was added in 25 milliliter aliquots. After each aliquot addition, the mixture was placed in vacuo for five minutes. After the final aliquot addition, the reaction mixture was held for two hours under a nitrogen blanket and then placed in vacuo to remove the cyclohexane. The resultant pulverulent residue was the caprolactam magnesium bromide reaction product.

EXAMPLE V

This Example is similar to Example I, above, with the exception that laurolactam was used instead of epsilon-caprolactam.

| Ingredients | Amount |
| --- | --- |
| laurolactam | 180 grams |
| ethyl magnesium bromide (2.85 Molar in ether) | 64 milliliters |

The ethyl magnesium bromide was added to the laurolactam continuously over a period of an hour at a temperature of 32° C. After the addition was complete, the reaction product was vacuum stripped leaving the laurolactam magnesium bromide reaction product as a pulverulent residue. The theoretical conversion of lactam monomer to reaction product was 20 mole percent.

EXAMPLE VI

This Example illustrates the preparation of a particulate organomagnesium compound according to the present invention. In this Example, the particulate active hydrogen-containing material is dispersed in cyclohexane prior to admixture with the organomagnesium halide.

| Ingredients | Amount |
| --- | --- |
| neopentyl glycol | 74 grams |
| cyclohexane | 200 grams |
| ethyl magnesium bromide (2.9 Molar in ether) | 50 milliliters |

The neopentyl glycol was agitated together with the cyclohexane until a dispersion was formed. Subsequently, the ethyl magnesium bromide was added over a thirty to sixty minute period while maintaining the temperature below 40° C. After the addition was complete, the cyclohexane was removed in vacuo leaving the neopentyl glycoxy magnesium bromide as a pulverulent residue. The theoretical conversion of hydroxy groups to oxymagnesium bromide groups was 10 percent.

EXAMPLE VII

This Example illustrates the preparation of a particulate organomagnesium compound according to the present invention.

| Ingredients | Amount |
| --- | --- |
| Bisphenol A | 162.7 grams |
| ethyl magnesium bromide (2.85 Molar in ether) | 50 milliliters |

The Bisphenol A was charged to a flask under a nitrogen atmosphere and stirred. While stirring, the ethyl magnesium bromide was added while maintaining the temperature below 50° C. After addition was complete, the reaction product was vacuum stripped leaving it as a pulverulent residue. The theoretical conversion of hydroxy groups to oxymagnesium bromide groups was 10 percent.

What is claimed is:

1. A process for the preparation of a pulverulent organomagnesium compound comprising bringing together into intimate admixture a particulate hydroxyl functional material with an organomagnesium-containing material at a temperature below the melting point of the hydroxyl functional mataerial but at a temperature sufficient to convert at least a portion of the hydroxyl functional material to said pulverulent organomagnesium compound.

2. The process of claim 1 wherein the admixture is carried out at or about ambient temperature.

3. The process of claim 1 wherein the particulate hydroxyl functional material is in essentially dispersed form in a diluent prior to admixture with the organomagnesium-containing material.

4. The process of claim 3 wherein the diluent is a non-solvent for the hydroxyl functional material.

5. The process of claim 4 wherein the diluent is cyclohexane.

6. The process of claim 1 wherein the organomagnesium-containing material is an organomagnesium halide.

7. The process of claim 6 wherein the organomagnesium halide is ethyl magnesium bromide.

* * * * *